United States Patent [19]

Buchanan et al.

[11] Patent Number: 5,538,834
[45] Date of Patent: Jul. 23, 1996

[54] BLOCKED PHOTOGRAPHICALLY USEFUL COMPOUNDS FOR USE WITH PEROXIDE-CONTAINING PROCESSES

[75] Inventors: J. Michael Buchanan; Jared B. Mooberry; John Texter, all of Rochester, N.Y.

[73] Assignee: Eastman Kodak Company, Rochester, N.Y.

[21] Appl. No.: 342,983

[22] Filed: Nov. 21, 1994

Related U.S. Application Data

[62] Division of Ser. No. 147,430, Nov. 5, 1993, abandoned, which is a continuation of Ser. No. 810,241, Dec. 19, 1991, abandoned.

[51] Int. Cl.$^6$ ............ G03C 7/305; G03C 7/407
[52] U.S. Cl. ............ 430/377; 430/373; 430/376; 430/380; 430/382; 430/447; 430/544; 430/955; 430/957; 430/958; 430/959; 430/943
[58] Field of Search ............ 430/367, 373, 430/943, 219, 222, 544, 955, 957, 958, 954, 241, 417, 423, 407, 432, 447, 376, 380, 382, 377

[56] References Cited

U.S. PATENT DOCUMENTS

| | | | |
|---|---|---|---|
| 3,230,083 | 1/1966 | Simon | 430/224 |
| 3,674,478 | 7/1972 | Grasshoff et al. | 96/3 |
| 3,935,262 | 1/1976 | Lestina et al. | 430/224 |
| 3,980,479 | 9/1976 | Fields et al. | 430/222 |
| 3,993,661 | 11/1976 | Grasshoff et al. | 260/308 D |
| 4,045,225 | 8/1977 | Shimamura et al. | 96/60 R |
| 4,278,750 | 7/1981 | Chen | 430/222 |
| 4,358,525 | 11/1982 | Mooberry et al. | 430/222 |
| 4,371,609 | 2/1983 | Kajiwara et al. | 430/373 |
| 4,469,780 | 9/1984 | Hirai et al. | 430/373 |
| 4,526,860 | 7/1985 | Kitchin | 430/373 |
| 4,554,243 | 11/1985 | Ono et al. | 430/222 |
| 4,629,683 | 12/1986 | Itoh et al. | 430/222 |
| 4,678,739 | 7/1987 | Kitaguchi et al. | 430/219 |
| 4,734,353 | 3/1988 | Ono et al. | 430/219 |
| 4,737,450 | 4/1988 | Hall et al. | 430/943 |
| 4,892,811 | 1/1990 | Yagihara et al. | 430/222 |
| 5,019,492 | 5/1991 | Buchanan et al. | 430/643 |
| 5,210,097 | 5/1993 | Texter et al. | 430/373 |
| 5,240,821 | 8/1993 | Texter et al. | 430/959 |
| 5,256,525 | 10/1993 | Southby et al. | 430/959 |

FOREIGN PATENT DOCUMENTS

| | | |
|---|---|---|
| 0394974 | 10/1990 | European Pat. Off. . |
| 61-77851 | 4/1986 | Japan . |
| 2056104 | 3/1981 | United Kingdom . |

OTHER PUBLICATIONS

62–187850, Patent Abstract of Japan, Aug. 17, 1987, vol. 12, No. 42.

62–147457, Patent Abstract of Japan, Jul. 1, 1987, vol. 11, No. 378.

*Primary Examiner*—Richard L. Shilling
*Attorney, Agent, or Firm*—Sarah Meeks Roberts; J. Lanny Tucker

[57] ABSTRACT

A method is disclosed for developing an image in a photographic element comprising a support, a silver halide emulsion containing an imagewise distribution of developable silver halide grains, and a blocked photographically useful compound comprising a photographically useful group and a blocking group capable of releasing the photographically useful group upon processing the photographic element in the presence of a peroxide, wherein the blocking group comprises an electrophilic group which is solely capable of undergoing a nucleophilic displacement reaction, the electrophilic group being bonded directly or through a releasable timing group to the photographically useful group, with the proviso that when the photographically useful group is a development inhibitor, the blocking group is bonded to the photographically useful group through at least one releasable timing group. The method comprises the step of contacting the photographic element with a processing solution comprising a peroxide.

19 Claims, No Drawings

5,538,834

BLOCKED PHOTOGRAPHICALLY USEFUL COMPOUNDS FOR USE WITH PEROXIDE-CONTAINING PROCESSES

This is a Divisional of U.S. application Ser. No. 08/147,430, filed Nov. 5, 1993, which is a Rule 62 Continuation of U.S. Ser. No. 810,241, filed 19 Dec. 1991, both now abandoned.

BACKGROUND OF THE INVENTION

This invention pertains to an improved method for processing a photographic element using peroxide-containing processing solutions, and more specifically to the use of improved blocked photographically useful compounds in the photographic elements which are so processed.

Recent developments in blocking and timing group chemistry have led to improvements in blocked photographically useful compounds as disclosed in U.S. Pat. No. 5,019,492. As described therein, photographically useful compounds comprise a photographically useful group, and a blocking group. The blocking group comprises two electrophilic groups, the less electrophilic of which is bonded directly or through a releasable timing group to the photographically useful group, which electrophilic groups are separated from each other by a substituted atom that enables a nucleophilic displacement reaction to occur with release of the photographically useful group upon processing in the presence of a dinucleophile, such as hydroxylamine or a peroxide.

Preferred blocked photographically useful compounds according to U.S. Pat. No. 5,019,492 are represented by the formula:

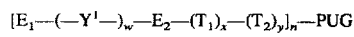

$$[E_1—(—Y^1—)_w—E_2—(T_1)_x—(T_2)_y]_n—PUG$$

wherein $E_1$ and $E_2$ are independently electrophilic groups, $E_1$ being more electrophilic than $E_2$; $T_1$ and $T_2$ are individually releasable timing groups; $Y^1$ is an unsubstituted or substituted atom, preferably a carbon or nitrogen atom, that provides a distance between $E_1$ and $E_2$ that enables a nucleophilic displacement reaction to occur with release of the PUG upon processing the photographic element containing the blocked photographically useful compound in the presence of a dinucleophile; PUG is a photographically useful group capable of being released upon processing the photographically useful compound; w, x and y are independently 0 or 1; and n is 1 or 2. These blocked photographically useful compounds are highly effective and very stable in photographic elements prior to processing with dinucleophiles.

β-Ketoester blocking groups have proven to be especially advantageous, particularly when the processing solution contains hydroxylamine. However, these blocking groups can be somewhat difficult and costly to prepare.

Environmental considerations as well as materials cost reduction have favored the use of hydrogen peroxide in the processing solution. Photographic elements with much lower levels of coated silver can be achieved if an amplifying bath containing aqueous alkaline hydrogen peroxide is used in the development process (the so-called "RX" process). The image intensification or amplification method is described, for example, in Japanese Laid-Open Application No. 61/77,851 and U.S. Pat. Nos. 4,526,860, 4,469,780, 4,371,609 and 4,045,225.

According to this method, a smaller amount of silver halide than usual is incorporated in the photographic material. This type of photographic material is referred to herein as a "low silver laydown" photographic material. The low silver laydown material is exposed and the silver halide is reduced imagewise to silver metal by a developing agent. An amplifying agent then is brought into contact with a developing agent in the presence of the resulting silver nuclei which act as a catalyst for the oxidation of the developing agent by the amplifying agent. The oxidized developing agent then reacts with couplers to form dye images.

Among known intensifying agents are peroxides, halogenous acids, iodoso compounds and cobalt (III) complexes, of which hydrogen peroxide is said to have higher amplification activity. For example, at page 406 of *History of Color Photography* by J. S. Friedman, there is described a process of oxidizing a p-phenylenediamine color developing agent with hydrogen peroxide in the presence of a silver catalyst.

The consumption of bleaching and fixing chemicals needed to remove silver/silver halide from the film is greatly reduced in low silver films. This results in decreased environmental impact as well as materials cost savings.

A need has therefore existed for highly stable blocked photographically useful compounds which are simply and economically prepared, and for photographic elements incorporating such compounds which can be developed so as to alleviate the problems identified above. In particular, it would be desirable to provide photographic elements incorporating blocked photographically useful compounds which can be processed using processing solutions containing peroxides, in order to reduce silver costs and the environmental impact of the development process.

SUMMARY OF THE INVENTION

These needs have been satisfied by providing a method for developing an image in a photographic element comprising a support, a silver halide emulsion containing an imagewise distribution of developable silver halide grains, and a blocked photographically useful compound comprising a photographically useful group and a blocking group capable of releasing the photographically useful group upon processing the photographic element in the presence of a peroxide, which comprises the step of contacting the photographic element with a processing solution comprising a peroxide. According to the invention, the blocking group comprises an electrophilic group which is the sole group capable of undergoing a nucleophilic displacement reaction. The electrophilic group is bonded directly or through at least one releasable timing group to the photographically useful group.

Preferably, the blocked photographically useful compound has the structure

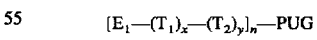

$$[E_1—(T_1)_x—(T_2)_y]_n—PUG$$

in which $E_1$ is an electrophilic group, $T_1$ and $T_2$ are individually releasable timing groups, PUG is a photographically useful group capable of being released upon processing the photographically useful compound, x and y are independently 0 or 1, and n is 1 or 2.

Particularly preferably, the blocking group is an acyl group. That is, the electrophilic group $E_1$ has the structure

where $R_1$ is, for example, an alkyl, alkoxy, aryl or aryloxy group which is unsubstituted or substituted with, for example, an alkoxy, halogen or amido group.

There has additionally been provided a photographic element comprising a support, a silver halide emulsion and a blocked photographically useful compound as described above, with the proviso that when said photographically useful group is a development inhibitor, said blocked photographically useful compound comprises at least two releasable timing groups.

In a particular embodiment, the blocked photographically useful compound has the preferred structure described above, with the proviso that when PUG is a development inhibitor, the product $n(x+y)$ is at least 2.

DETAILED DESCRIPTION OF PREFERRED EMBODIMENTS

It has now been discovered that blocked compounds including blocking groups according to the present invention, which are insufficiently reactive in the presence of hydroxylamine to be photographically useful, surprisingly and unexpectedly are much more reactive in the presence of peroxides. The compounds blocked according to the invention are sufficiently reactive to be photographically useful in photographic elements that are processed using processing solutions that contain peroxides. Thus, the method of the invention provides the advantages of reduced silver costs and reduced environmental impact compared to conventional processing methods.

Related inventions and embodiments are described in commonly assigned U.S. Ser. Nos. 07/810,322 (now U.S. Pat. No. 5,210,007), 07/810,232 (now U.S. Pat. No. 5,240,821), and 07/810,944 (now U.S. Pat. No. 5,256,525), filed Dec. 19, 1991, and incorporated in their entireties by reference.

As used herein, an "electrophilic group which is the sole group capable of undergoing a nucleophilic displacement reaction" denotes a group having only one electrophilic moiety that is capable of reacting with a nucleophile such that the bond between the blocking group and the remainder of the blocked photographically useful compound is cleaved. In other words, the blocking group contains only one electrophilic moiety that participates in the displacement reaction.

Of the foregoing electrophilic groups, simple acyl groups are particularly preferred. Simple acyl groups are those in which the acyl moiety —CO—, or R—CO—, is the sole electrophilic moiety that participates in the nucleophilic displacement reaction. This contrasts with, for example, the "β-ketoesters" (strictly, β-ketoacyl groups) of U.S. Pat. No. 5,019,492, in which both a keto group and an acyl group (that is, both electrophilic groups) participate in the displacement reaction. Simple acyl groups in particular have the advantage that they are relatively easy and inexpensive to produce.

Preferred acyl groups include acetyl, propionyl, pivalyl, butyryl, isobutyryl, pentanoyl, hexanoyl, etc.

As used herein, the term "photographically useful group (PUG)" refers to any group that can be used in a photographic material and that can be released from the blocking group as described. It refers to the part of the blocked photographically useful compound other than the blocking group (and the optional timing group). The PUG can be, for example, a photographic dye or photographic reagent. A photographic reagent herein is a moiety that upon release further reacts with components in the photographic element. Such photographically useful groups include, for example, couplers (such as image dye-forming couplers, development inhibitor releasing couplers, competing couplers, polymeric couplers and other forms of couplers), development inhibitors, bleach accelerators, mobile and immobile dyes, dye precursors, developing agents (such as competing developing agents, dye-forming development agents, developing agent precursors, and silver halide developing agents), silver ion fixing agents, silver halide solvents, silver halide complexing agents, image toners, pre-processing and post-processing image stabilizers, hardeners, tanning agents, fogging agents, antifoggants, ultraviolet radiation absorbers, nucleators, chemical and spectral sensitizers or desensitizers, surfactants, and precursors thereof, as well as other addenda known to be useful in photographic materials.

The PUG can be present in the photographically useful compound as a preformed species or as a precursor. For example, a preformed development inhibitor may be bonded to the blocking group or the development inhibitor may be attached to one or two timing groups that are released at particular times and locations in the photographic material. The PUG may be, for example, a preformed dye or a compound that forms a dye after release from the blocking group.

Illustrative examples of useful PUG's that can be blocked with the blocking groups as described are as follows:

I. Couplers

A. Image dye-forming couplers: Illustrative couplers include cyan, magenta and yellow image dye-forming couplers that are known in the photographic art. Illustrative cyan dye-forming couplers that can comprise the blocking group as described include, for example, those described in U.S. Pat. Nos. 2,367,531; 2,423,730; 2,474,293; 2,772,162; 2,895,826; 3,002,836; 3,034,892; 3,041,236; and 4,333,999. Illustrative magenta dye-forming couplers that can comprise the blocking group as described include those disclosed in, for example, U.S. Pat. Nos. 2,311,082; 2,343,703; 2,369,489; 2,600,788; 2,908,573; 3,062,653; 3,152,896; and 3,519,429. Illustrative yellow dye-forming couplers that can contain the blocking group as described include those described in, for example, U.S. Pat. Nos. 2,298,443; 2,407,210; 2,875,057; 3,048,194; 3,265,506; and 3,447,928.

B. Illustrative couplers that form colorless products upon reaction with oxidized color developing agents and can contain the blocking group as described include those disclosed in, for example, U.S. Pat. Nos. 3,632,345; 3,928,041; 3,958,993; 3,961,959; and U.K. Patent No. 861,138.

C. Illustrative couplers that form black dyes upon reaction with oxidized color developing agents and that can contain the blocking group as described include those disclosed in, for example, U.S. Pat. Nos. 1,939,231; 2,181,944; 2,333,106; and 4,126,461; German OLS No. 2,644,194 and German OLS No. 2,650,764.

D. Illustrative couplers that are development inhibitor releasing couplers (DIR couplers) and can contain the blocking group as described include those described in, for example, U.S. Pat. Nos. 3,227,554; 3,384,657; 3,615,506; 3,617,291; 3,733,201; 4,248,962; and U.K. 1,450,479. Preferred development inhibitors as PUG's are heterocyclic compounds, such as mercaptotetrazoles, mercaptotriazoles, mercaptooxadiazoles, selenotetrazoles, mercaptobenzothiazoles, selenobenzothiazoles, mercaptobenzoxazoles, selenobenzoxazoles, mercaptobenzimidazoles, selenobenzimidazoles, benzotriazoles, benzodiazoles and 1,2,4-triazoles, tetrazoles, and imidazoles.

II. Dyes and Dye Precursors

Useful dyes and dye precursors include azo, azomethine, methine, azopyrazolone, indoaniline, indophenol, anthraquinone, triarylmethane, alizarin, nitro, quinoline, indigoid, oxanol, and phthalocyanine dyes and precursors of such dyes, such as leuco dyes, tetrazolium salts or shifted dyes. These dyes can be metal complexed or metal complexable. Representative patents describing such dyes are U.S. Pat. Nos. 3,880,568; 3,931,144; 3,932,380; 3,932,381; and 3,942,987.

III. Developing Agents

Developing agents released can be color developing agents, black-and-white developing agents and cross-oxidizing developing agents. They include aminophenols, phenylenediamines, hydroquinones and pyrazolidones. Representative patents describing such developing agents are U.S. Pat. Nos. 2,108,243; 2,193,015; 2,289,367; 2,304,953; 2,592,364; 2,743,279; 2,751,297; 2,753,256; 2,772,282; 3,656,950; and 3,658,525. Developing agents disclosed in copending and commonly assigned U.S. Ser. No. 07/810,232, filed Dec. 19, 1991, are particularly preferred.

IV. Bleach Inhibitors

Representative bleach inhibitors that can be blocked as described include the illustrative bleach inhibitors described in, for example, U.S. Pat. Nos. 3,705,801; 3,715,208 and German OLS No. 2,405,279.

Preferred PUG's are also described in U.S. Pat. No. 5,019,492, which is hereby incorporated by reference.

In a preferred embodiment of the present invention, the PUG is a developer precursor. Preferred developer precursors according to the invention include p-phenylenediamines and aminophenols, and are given below in Tables I and II, respectively. These developer precursors according to the invention are prepared by well-known techniques, such as those described in U.S. Pat. No. 5,019,492, and copending and commonly assigned U.S. Ser. No. 07/810,232, filed Dec. 19, 1991, as well as in U.S. patent application Ser. No. 07/700,006, U.S. Pat. No. 3,342,599, U.S. Pat. No. 4,060, 418, and U.S. Pat. No. 4,157,915, the disclosures of each of which are hereby incorporated by reference.

TABLE I

[Structure: Z—C(=O)—O—[phenyl with X]—CH$_2$—O—C(=O)—NH—[phenyl with CH$_3$]—N(CH$_2$CH$_3$)(CH$_2$CH$_2$NHSO$_2$CH$_3$)]

|   | Z | X |
|---|---|---|
| 1 | —C(CH$_3$)$_3$ | —NHSO$_2$CH$_2$ |
| 2 | [phenyl with NHSO$_2$CH$_3$] | —H |
| 3 | —CH(CH$_3$)$_2$ | —NHCO(CH$_2$)$_3$CO$_2$H |
| 4 | —CH(CH$_3$)$_2$ | —NHSO$_2$CH$_3$ |
| 5 | —CH$_2$CH$_3$ | —NHCO(CH$_2$)$_3$CO$_2$H |
| 6 | —CH$_2$CH$_3$ | —NHCO—[phenyl]—NHSO$_2$CH$_3$ |
| 7 | —CH$_2$CH$_3$ | —NHSO$_2$CH$_3$ |

[Structure: Z—C(=O)—O—[phenyl with X]—CH(Y)—O—C(=O)—NH—[phenyl with CH$_3$]—N(CH$_2$CH$_2$)(CH$_2$CH$_2$—Y)]

|   | Y | Z | Y | X |
|---|---|---|---|---|
| 8 | —H | —CH$_2$CH$_3$ | —NHSO$_2$CH$_3$ | —NH—CO—[phenyl]—CO$_2$H |
| 9 | —H | —CH$_2$CH$_3$ | —OH | —NH—CO—[phenyl]—CO$_2$H |

TABLE I-continued

| | | | | |
|---|---|---|---|---|
| 10 | —H | —CH$_2$CH$_3$ | —H | —NH—CO—C$_6$H$_4$—CO$_2$H |
| 11 | —H | —CH$_3$ | —NHSO$_2$CH$_3$ | —NH—CO—C$_6$H$_4$—CO$_2$H |
| 12 | —H | —CH$_2$CH$_2$CH$_3$ | —NHSO$_2$CH$_3$ | —NH—CO—C$_6$H$_4$—CO$_2$H |
| 13 | —H | —CH(CH$_3$)$_2$ | —NHSO$_2$CH$_3$ | —NH—CO—C$_6$H$_4$—CO$_2$H |
| 14 | —H | —CH$_2$CH$_3$ | —NHSO$_2$CH$_3$ | —N(CH$_3$)—CO—C$_6$H$_4$—CO$_2$H |
| 15 | —H | —CH$_2$CH$_3$ | —NHSO$_2$CH$_3$ | —NH—CO—CH(C$_{12}$H$_{25}$-n)—O—C$_6$H$_4$—CO$_2$H |
| 16 | —CH$_3$ | —CH$_2$CH$_3$ | —NHSO$_2$CH$_3$ | —NH—CO—C$_6$H$_4$—NHSO$_2$CH$_3$ |
| 17 | —H | —CH(CH$_3$)$_2$ | —OH | —H |
| 18 | —H | —C$_6$H$_4$—SO$_2$NH$_2$ | —NHSO$_2$CH$_3$ | —H |
| 19 | —H | —CH(CH$_2$CH$_3$)—O—C$_6$H$_4$—CO$_2$K | —NHSO$_2$CH$_3$ | —H |
| 20 | —H | —CH$_2$—C$_6$H$_4$—NHSO$_2$CH$_3$ | —NHSO$_2$CH$_3$ | —H |

TABLE II

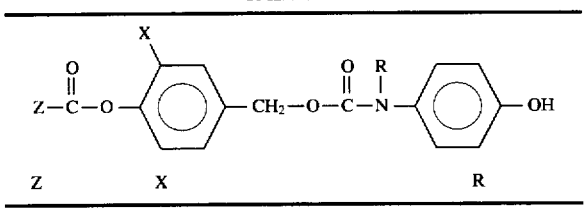

| | Z | X | R |
|---|---|---|---|
| 21 | —CH$_2$CH$_3$ | —NH—CO—C$_6$H$_4$—CO$_2$H | —CH$_3$ |
| 22 | —CH(CH$_3$)$_2$ | —NHSO$_2$CH$_3$ | —CH$_2$CH$_3$ |

TABLE II-continued

| | | | |
|---|---|---|---|
| 23 | —CH(CH$_3$)$_2$ | —NH—CO—C$_6$H$_4$—CO$_2$H | —CH$_3$ |
| 24 | —CH(CH$_3$)$_2$ | —NH—CO—C$_6$H$_4$—CO$_2$H | —H |

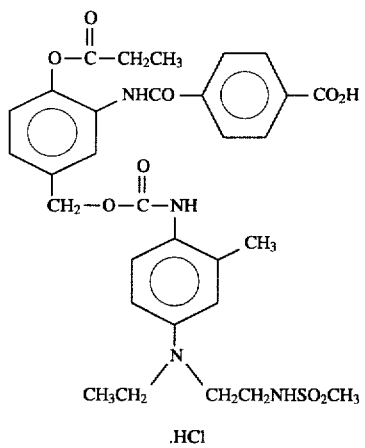

| | Z | X | R$_1$ | R$_2$ |
|---|---|---|---|---|
| 25 | —CH$_3$ | —OCH$_3$ | —CH$_2$CH$_3$ | —CH$_2$CH$_3$ |
| 26 | —CH(CH$_3$)$_2$ | —H | —CH$_2$CH$_2$OH | —CH$_2$CH$_3$ |
| 27 | —CH$_2$CH$_3$ | —NHSO$_2$CH$_3$ | —CH$_3$ | —CH$_3$ |
| 28 | —CH$_2$CH$_3$ | —H | —CH$_2$CH$_3$ | —CH$_2$CH$_3$ |

Additional preferred photographically useful groups include the following:

Developing Agents:

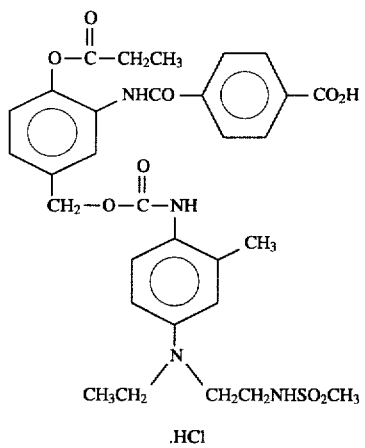

29

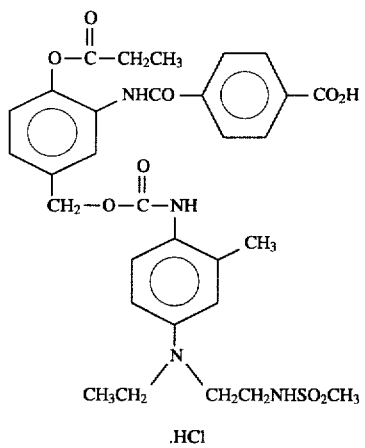

30

Filter Dyes:

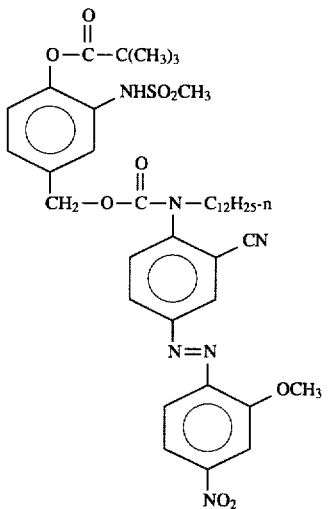

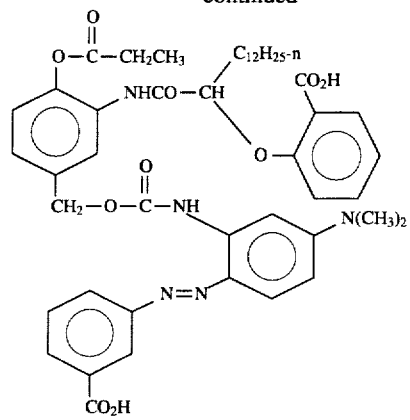

31

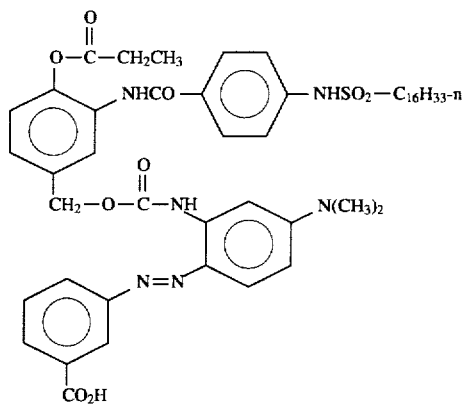

32

Bleach Accelerators:

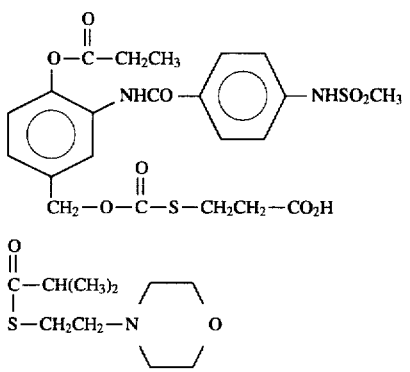

33

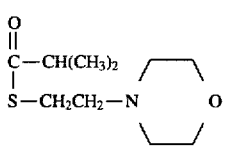

34

Development Accelerators:

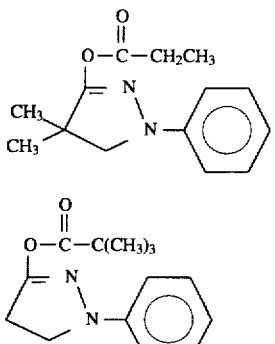

35

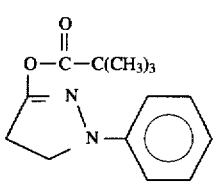

36

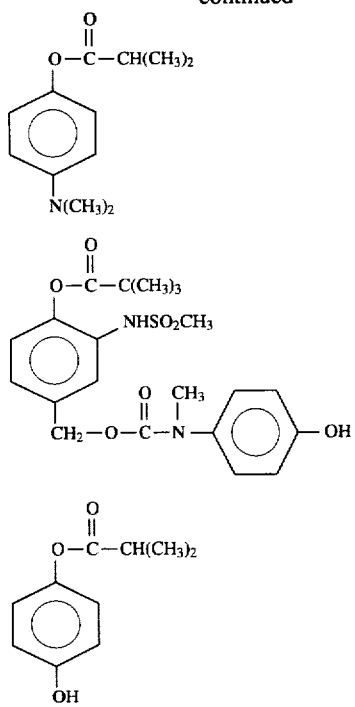

Exemplary timing groups are disclosed in U.S. Pat. Nos. 4,248,962; 4,741,994; 4,772,537; 4,985,336; and 5,019,492, the disclosures of which are incorporated by reference.

Both the blocking group and the timing group according to the invention can contain one or more substituents. Such substituents can be added, for example, to control the aqueous solubility of the developer precursor. Exemplary substituents can include halogen, alkyl, aryl, heterocyclic, cyano, alkoxy, aryloxy, acyl, acylamino, anilino, ureido, alkylthio, arylthio, alkoxycarbonylamino, sulfonamido, unsubstituted or substituted carbamoyl, sulfamoyl, sulfonyl, alkyoxycarbonyl, heterocyclic oxy, acyloxy, carbamoyloxy, aryloxycarbonylamino, imido, heterocyclic thio, sulfinyl, phosphonyl, aryloxycarbonyl, alkylsulfonyl, arylsulfonyl, hydroxy, carboxy, and sulfo groups, as well as others known to those skilled in the art.

Both the timing and blocking groups can be unballasted or ballasted. In other words, at least one of timing and blocking groups can include a group of such molecular size and configuration as to render the present compound nondiffusible as described, for example, in U.S. Pat. Nos. 4,420,556 and 4,923,789. Advantageous ballast groups include alkyl and aryl groups having from about 8 to 32 carbon atoms.

The blocked photographically useful compounds may be located in any layer of the photographic element that is readily accessible to processing fluid during the development process. The amounts used will depend on the type of photographically useful compound, and will be routinely determined in known manners by the skilled artisan. For example, in the case in which the blocked PUG is a color developer, it will preferably be coated in a photographic element at a molar equivalent ranging from about $10^{-5}$ mol/m$^2$ to $5 \times 10^{-2}$ mol/m$^2$. In the case in which the blocked PUG is a development inhibitor, it will preferably be coated in a photographic layer at a level corresponding to about 0.0001 to 0.1 times the molar amount of image-dye forming coupler coated in that layer. In the case in which the blocked PUG is a bleach accelerator, it will preferably be coated at a molar equivalent level corresponding to about $5 \times 10^{-5}$ to $10^{-2}$ times the molar amount of silver (as silver halide) coated in the element. Similarly, in the case in which the blocked PUG is a development accelerator, it will preferably be coated at a molar equivalent level corresponding to about $10^{-5}$ to $5.0 \times 10^{-2}$ times the molar amount of silver (as silver halide) coated in the element.

Peroxides that are preferred components of processing solutions for use in the method according to the invention have the structure $$R_2\text{---OOH}$$

in which $R_2$ is H or an unsubstituted or substituted alkyl, aryl, alkaryl, aralkyl or acyl group. $R_2$ can also be a sulfonyl, oxycarbonyl or borate group, or any group in general which hydrolyzes readily in alkaline solution to yield hydrogen peroxide. Hydrogen peroxide is the particularly preferred reagent (hydrogen peroxide is present as a salt in alkaline solution, that is, in the form H—O—OM$^+$, which is the active species).

Additional compounds that are preferred components of processing solutions for use in the method according to the invention have the structure $$R_3\text{---O---O---}R_4$$

in which each of $R_3$ and $R_4$ independently is an unsubstituted or substituted alkyl, aryl, alkaryl, aralkyl, sulfonyl, oxycarbonyl or borate group, or any group in general which is hydrolyzable in alkaline solution to yield the peroxy anion, and in which at least one of $R_3$ and $R_4$ is a group that is hyarolyzable in alkaline solution to yield the peroxy anion. Disodium peroxydicarbonate is a preferred reagent.

In the following discussion of suitable materials for use in the photographic elements processed according to the invention, reference will be made to Research Disclosure, December 1989, Item 308119, published by Kenneth Mason Publications Ltd., Emsworth, Hampshire PO10 7DQ, U.K., the disclosures of which are incorporated in their entireties herein by reference. This publication will be identified hereafter as "Research Disclosure".

The support of the element of the invention can be any of a number of well known supports for photographic elements. These include polymeric films, such as cellulose esters (for example, cellulose triacetate and diacetate) and polyesters of dibasic aromatic carboxylic acids with divalent alcohols (such as polyethylene terephthalate), paper, and polymer-coated paper.

The photographic elements according to the invention can be coated on the selected supports as described in Research Disclosure Section XVII and the references cited therein.

The radiation-sensitive layer of a photographic element according to the invention can contain any of the known radiation-sensitive materials, such as silver halide, or other light sensitive silver salts. Silver halide is preferred as a radiation-sensitive material. Silver halide emulsions can contain, for example, silver bromide, silver chloride, silver iodide, silver chlorobromide, silver chloroiodide, silver bromoiodide, or mixtures thereof. The emulsions can include coarse, medium, or fine silver halide grains bounded by 100, 111, or 110 crystal planes.

The silver halide emulsions employed in the elements according to the invention can be either negative-working or positive-working. Suitable emulsions and their preparation are described in Research Disclosure Sections I and II and the publications cited therein.

Also useful are tabular grain silver halide emulsions. In general, tabular grain emulsions are those in which greater than 50 percent of the total grain projected area comprises tabular grain silver halide crystals having a grain diameter and thickness selected so that the diameter divided by the mathematical square of the thickness is greater than 25, wherein the diameter and thickness are both measured in microns. An example of tabular grain emulsions is described in U.S. Pat. No. 4,439,520.

Suitable vehicles for the emulsion layers and other layers of elements according to the invention are described in Research Disclosure Section IX and the publications cited therein.

The radiation-sensitive materials described above can be sensitized to a particular wavelength range of radiation, such as the red, blue, or green portions of the visible spectrum, or to other wavelength ranges, such as ultraviolet, infrared, X-ray, and the like. Sensitization of silver halide can be accomplished with chemical sensitizers such as gold compounds, iridium compounds, or other group VIII metal compounds, or with spectral sensitizing dyes such as cyanine dyes, merocyanine dyes, or other known spectral sensitizers. Exemplary sensitizers are described in Research Disclosure Section IV and the publications cited therein.

Multicolor photographic elements according to the invention generally comprise a blue-sensitive silver halide layer having a yellow color-forming coupler associated therewith, a green-sensitive layer having a magenta color-forming coupler associated therewith, and a red-sensitive silver halide layer having a cyan color-forming coupler associated therewith. Color photographic elements and color-forming couplers are well-known in the art.

The elements according to the invention can include couplers as described in Research Disclosure Section VII, paragraphs D, E, F and G and the publications cited therein. These couplers can be incorporated in the elements and emulsions as described in Research Disclosure Section VII, paragraph C and the publications cited therein.

A photographic element according to the invention, or individual layers thereof, can also include any of a number of other well-known additives and layers. These include, for example, optical brighteners (see Research Disclosure Section V), antifoggants and image stabilizers (see Research Disclosure Section VI), light-absorbing materials such as filter layers of intergrain absorbers, and light-scattering materials (see Research Disclosure Section VIII), gelatin hardeners (see Research Disclosure Section X), oxidized developer scavengers, coating aids and various surfactants, overcoat layers, interlayers, barrier layers and antihalation layers (see Research Disclosure Section VII, paragraph K), antistatic agents (see Research Disclosure Section XIII), plasticizers and lubricants (see Research Disclosure Section XII), matting agents (see Research Disclosure Section XVI), antistain agents and image dye stabilizers (see Research Disclosure Section VII, paragraphs I and J), development-inhibitor releasing couplers and bleach accelerator-releasing couplers (see Research Disclosure Section VII, paragraph F), development modifiers (see Research Disclosure Section XXI), and other additives and layers known in the art.

Photographic elements according to the invention can be exposed to actinic radiation, typically in the visible region of the spectrum, to form a latent image as described in Research Disclosure Section XVIII, and then processed to form a visible dye image as described in Research Disclosure Section XIX, Part G.

A negative image can be developed by color development using one or more of the aforementioned peroxides. A positive image can be developed by first developing with a nonchromogenic developer, then uniformly fogging the element, and then developing by a process employing one or more of the aforementioned peroxides. If the material does not contain a color-forming coupler compound, dye images can be produced by incorporating a coupler in the developer solutions.

Development is followed by the conventional steps of bleaching, fixing, or bleach-fixing (blixing), to remove silver and silver halide, washing and drying. Bleaching and fixing can be performed with any of the materials known to be used for that purpose. Bleach baths generally comprise an aqueous solution of an oxidizing agent such as water soluble salts and complexes of iron (III) (such as potassium ferricyanide, ferric chloride, ammonium or potassium salts of ferric ethylenediaminetetraacetic acid), water-soluble dichromates (such as potassium, sodium, and lithium dichromate), and the like. Fixing baths generally comprise an aqueous solution of compounds that form soluble salts with silver ions, such as sodium thiosulfate, ammonium thiosulfate, potassium thiocyanate, sodium thiocyanate, thioureas, and the like.

The invention is further illustrated by the following examples, without being limited thereby.

Synthesis Example 1: Synthesis of Compound 6

The synthesis is illustrated in the following reaction scheme:

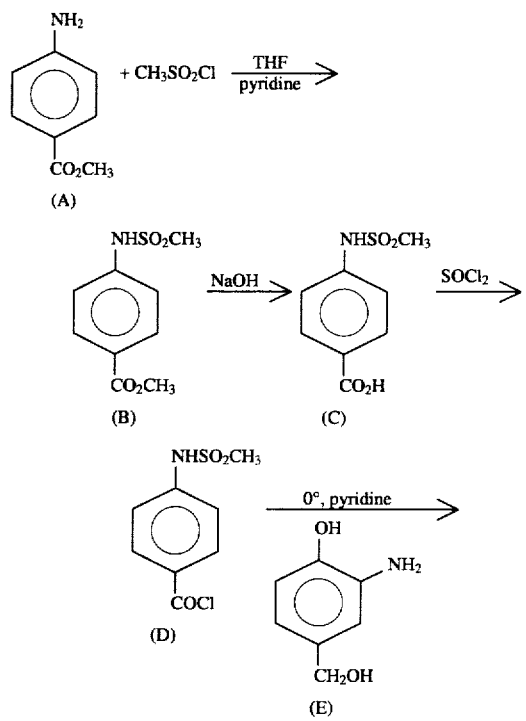

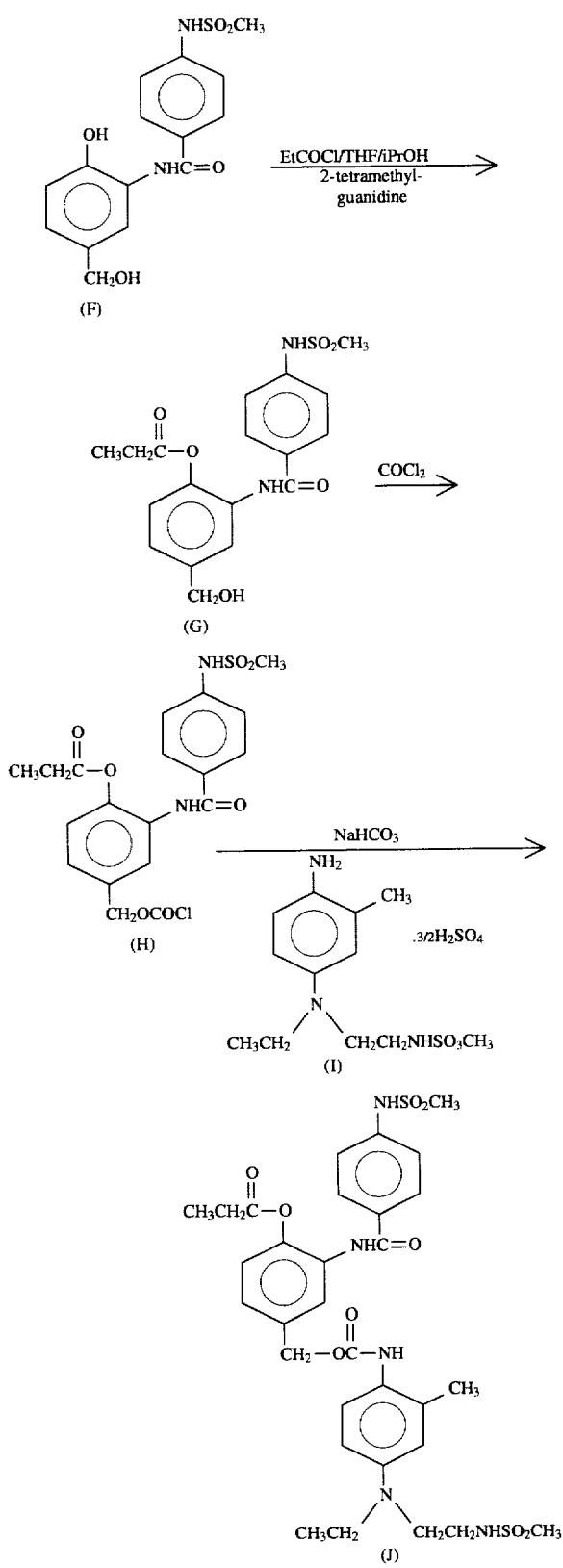

before adding methanesulfonyl chloride (24.2 ml, 0.31 tool, in 30 ml THF) slowly over 5 minutes. After stirring for about 20 minutes, the mixture was made acidic with excess 1N HCl and saturated NaCl. Product was obtained by extraction with ethyl acetate, drying over MgSO$_4$, and concentration in a rotary evaporator to a solid. Ester (B) (45 g) was obtained by slurrying this solid in heptane and filtering. Saponification of this ester (56.8 g, 0.25 mole) with NaOH (96 g of a 50% aqueous solution) in 240 ml of water at 50° C. was complete in about 10 minutes. Acidification with aqueous HCl precipitated carboxylic acid (C), which was filtered, washed with water, and air dried to yield 42 g.

The carboxylic acid (C) (54.7 g, 0.254 mole) was refluxed in a mixture of methylene chloride (335 ml), thionyl chloride (335 ml) and dimethylformamide (1 ml) for one hour. Solvents were distilled off under vacuum and residual thionyl chloride was chased with 500 ml of methylene chloride. The solid residue was slurried in 1:1 mixture of heptane: methylene chloride, filtered, redissolved in THF, refiltered, and air dried to solid acid chloride (D) (59.3 g).

3-Amino-4-hydroxybenzyl alcohol (E) (14.4 g., 0.104 mole), prepared by reduction of the corresponding nitro alcohol, as described in U.S. Pat. No. 4,840,884, was completely dissolved in pyridine (90 ml) in a 500 ml round bottomed flask fitted with addition funnel, thermometer, and mechanical stirrer. After cooling in ice, the mixture was treated with a solution of acid chloride (D) (24.3 g, 0.104 mole) in about 60 ml of THF, dropwise over about 10 minutes. The mixture was then allowed to warm slowly to room temperature over 45 minutes before diluting with excess aqueous HCl to precipitate the product. It was filtered, washed with water, and air dried to yield 29.5 g of amide (F) (12 g, 0.0357 mole). Amide (F) was dissolved in a mixture of isopropanol (150 ml) and tetramethylguanidine (8.2 g, 0.071 mole), cooled in a ice bath, and treated with propionyl chloride (3.1 ml, 0.0357 mole) in about 10 ml of THF, dropwise over a few minutes before allowing the mixture to stir for 20 minutes. The mixture was diluted with 100 ml of saturated NaCl, 70 ml of water, and 30 ml of 2N HCl before extracting the ester into ethyl acetate. The extracts were concentrated to yield crystalline solid (G) (10.5 g, 0.0268 mole). All of ester (G) was stirred at room temperature with a mixture of THF (50 ml), methylene chloride (50 ml), and phosgene (62 ml of 1.6M solution in toluene, 0.1 mole) for 4 hours. The mixture was then concentrated at 35° C. under vacuum to yield white solid chloroformate (H) which was used immediately.

Color developer (I) (17.4 g, 0.024 mole), sodium bicarbonate (13.4 g, 0.04 mole), methylene chloride (80 ml), and water (1000 ml) were combined in a round bottomed flask cooled in ice and stirred vigorously until all the solids were dissolved (gas evolution). All of chloroformate (H) (0.027 mole) was added. The mixture was stirred vigorously for 10 minutes and then allowed to separate into two phases. The organic phase was washed with aqueous acetic acid (pH about 3) to remove excess developer and then concentrated to a syrup which crystallized from ethyl acetate. White solid blocked developer (J) (15.1 g; Compound 6) was obtained.

Commercially available methyl p-aminobenzoate (A) (46.8 g, 0.31 mole) was dissolved in a mixture of THF (150 ml) and pyridine (60 ml). The mixture was cooled in ice

Synthesis Example 2: Preparation of Compound 30

The synthesis is illustrated in the following reaction scheme:

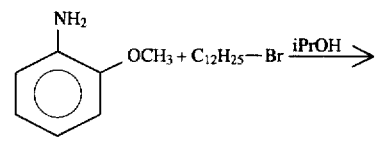

(K)

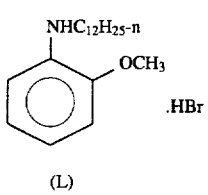
.HBr (L)

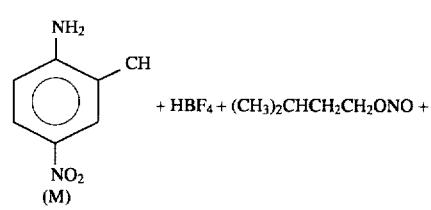

+ HBF₄ + (CH₃)₂CHCH₂CH₂ONO +

(M)

(L) $\xrightarrow[\text{HOAc}]{0°}$

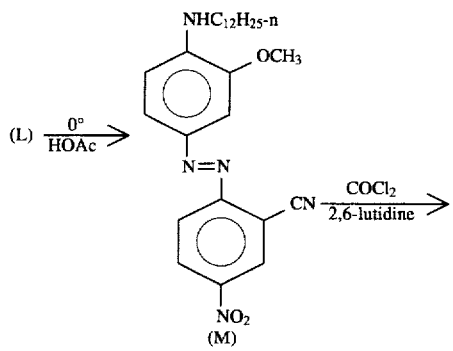

(M)

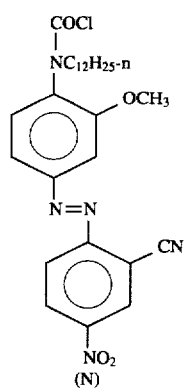

(N)

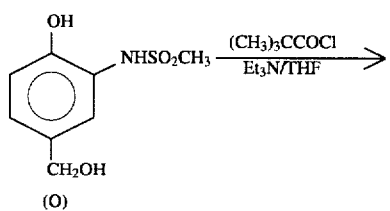

(O)

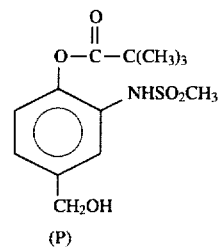

(P)

(P) + (N) $\xrightarrow[\text{DBU}]{\text{DMAP}}$

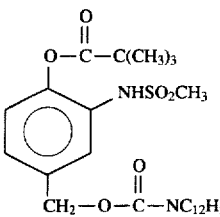

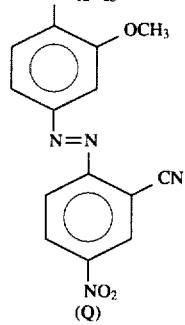

(Q)

O-anisidine (K) (23 ml, 0.2 mole), 1-bromododecane (51 g, 0.2 mole), and isopropyl alcohol (100 ml) were heated at reflux temperature for 16 hr. Isopropanol was removed by distillation and the residue was diluted with ether/heptane. A small amount of anisidine hydrobromide was removed by filtration before concentrating the filtrate and diluting with heptane. Alkylated product (L) (36 g, 50%) was obtained as white crystals.

2-Amino-5-nitrobenzonitrile (M) (16.3 g, 0.1 mole), fluoroboric acid (49% in water, 45 ml), and acetic acid (300 ml) were stirred at room temperature while adding isopentyl nitrite (11.7 g, 0.1 mole). This mixture was then warmed to 40° C. for about 5 minutes until a homogeneous solution was formed. This mixture was cooled in ice while a solution of coupler (L) (37.2 g, 0.1 mole) in a mixture of tetrahydrofuran (80 ml), acetic acid (100 ml), and water (20 ml) was added slowly. Sodium acetate (41 g) and a few chunks of ice were added and the mixture was allowed to warm slowly to room temperature overnight. The mixture was diluted with water (300 ml), stirred 30 minutes, and filtered. The crude dye was washed with methanol and then recrystallized twice from dichloromethane/methanol to obtain 12 g of purified dye (M).

Dye (M) (9.3 g, 0.02 mole) was treated with phosgene (10 ml of a 2M solution in toluene, 0.02 mole) and 2,6-lutidine (4.3 g, 0.04 mole) in dichloromethane (150 ml) solution. After 30 minutes at room temperature, the mixture was washed with cold aqueous HCl, then with water, dried over MgSO₄, and concentrated to syrupy carbamyl chloride product (N) (12.4 g).

3-Methylsulfonamido-4-hydroxybenzyl alcohol (O) (described in U.S. Pat. No. 4,840,884, 6.5 g, 0.03 mole), triethylamine (10 ml, 0.07 mole), and tetrahydrofuran (60 ml) were stirred at −20° C. while adding slowly a solution of pivalyl chloride (3.6 g, 0.03 mole in 30 ml of dichloromethane). The mixture was warmed to room temperature, diluted with dichloromethane, washed with aqueous HCl, aqueous bicarbonate, and then with water before drying over $MgSO_4$ and concentrating to syrupy benzyl alcohyl compound (P) (8.4 g).

Carbamyl chloride (N) (6.2 g, 0.01 mole) and benzyl alcohol (P) (3 g, 0.01 mole) were dissolved in 20 ml of dichloromethane and treated with dimethylaminopyridine (1.2 g, 0.01 mole) and diazabicycloundecane (DBU) (3 g, 0.02 mole). After 40 minutes the mixture was diluted with dichloromethane, washed with aqueous HCl, dried, and concentrated to a syrup. The crude product was chromatographed on silica gel twice using 3:1 heptane:ethyl acetate and then 5:1 toluene:ethyl acetate as eluents to yield (Q) (2 g; compound 30).

EXAMPLE 1

In order to demonstrate the enhancement of ester cleavage rate in solution due to the presence of hydrogen peroxide, p-nitrophenyl pivalate and compound 30 were contacted with processing solutions without and with the addition of hydrogen peroxide. Results are shown in Table III:

TABLE III

| Ester | $t_{1/2}$ (sec)$^c$, no $H_2O_2$ | $t_{1/2}$ (sec)$^c$, 0.1M $H_2O_2$ |
|---|---|---|
| p-nitrophenyl pivalate$^a$ | 5700 | 0.68 |
| compound 30$^b$ | >6000 | 18 |

$^a$5% $CH_3CN$ aqueous solution
$^b$3% TX-100 [α-(4-(1,1,3,3,)-tetramethylbutyl)phenyl)-ω-hydroxy-poly(oxy-1,2-ethanediyl)] non-ionic surfactant micellar solution
$^c$pH 10 solution, 25° C.

As is apparent, the addition of hydrogen peroxide dramatically increases the rate of ester cleavage above that normally encountered in pH 10 solution.

EXAMPLE 2

To demonstrate the utility of a non-light sensitive photographic layer containing a ballasted blocked filter dye according to the invention, filter dye compound 32 was dispersed in twice its weight of N,N-diethyldodecanamide and coated on a film support in format shown below:

| DOC FILTER DYE LAYER | Gelatin (2700 mg/m$^2$) Gelatin (3780 mg/m$^2$) compound 32 (197 mg/m$^2$) bis(vinylsulfonylmethyl)ether hardener (60 mg/m$^2$) |
|---|---|
| FILMBASE | polyacetate-butyrate |

Coating strips were suspended in a flow cell while alkaline buffer solutions at 40° C. were passed through it. As deblocking proceeded, the yellow color of the strips was reduced as the water-soluble filter dye was released and washed out of the film.

Reaction rates are tabulated in Table IV below.

TABLE IV

| Buffer solution | % reaction after 400 sec. | $t_{1/2}$ (sec.) |
|---|---|---|
| pH 10, no $H_2O_2$ | 3 | (very long) |
| pH 10, 0.2 N $H_2O_2$ | 77 | 220 |
| pH 10.7, no $H_2O_2$ | 31 | 780 |
| pH 10.7, 0.2 N $H_2O_2$ | 100 | 70 |

As shown in the table, hydrogen peroxide is effective in accelerating ester cleavage and release of dye from an immobile, ballasted filter dye in a film matrix.

Coatings containing compound 32 as described above were also subjected to accelerated keeping tests to determine raw stock stability. The coatings showed good storability, with greater than 93% recovery after Storage for 2 weeks at 50° C. and 50% relative humidity.

EXAMPLES 3–5

Blocked p-phenylenediamine developing agents 1, 3 and 6 were incorporated in photographic elements and evaluated for image dye formation activity and stability under storage conditions. The photographic elements were prepared as follows. The developing agents were dissolved in a high vapor pressure organic solvent (ethyl acetate for compounds 1 and 6, cyclohexanone for compound 3). The solutions were subsequently emulsified in aqueous gelatin using Alkanol-XC (Du Pont) as a dispersing aid. The dispersions were formulated such that the developing agents were initially present at 3% by weight, gelatin at 4% by weight and Alkanol-XC at 0.4% by weight. The initial slurries were emulsified by passing the mixtures through a colloid mill using known procedures. The organic solvents were then removed by evaporation.

The dispersions were costed on a film support in the format shown below:

| DOC DEVELOPER LAYER | Gelatin (1080 mg/m$^2$) Gelatin (2690 mg/m$^2$) developer dispersion (1.83 × 10$^{-3}$ mol/m$^2$) cyan coupler A (1080 mg/m$^2$) red-sensitive AgCl emulsion (32 mg/m$^2$ as AgCl) |
|---|---|
| FILMBASE | titania-tinted paper |

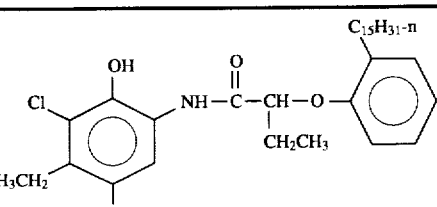

Coupler A

Sets of strips were incubated for 1 week at 100° F. and 50% relative humidity, and then evaluated by high performance liquid chromatography for amount of retained blocked developing agent. Sensitometry was obtained for step-tablet white-light exposures by contacting the strips with an activator solution at 77° F. The activator solution had the following composition:

| | |
|---|---|
| potassium carbonate | 50 g/l |
| hydrogen peroxide | 0.6% (w/w) |
| ANTICAL #5 (1-hydroxyethyl-1,1-diphosphonic acid) | 1 g/l |
| ANTICAL #8 (diethylenetriamine pentaacetic acid) | 1 g/l |
| KODAK PHOTO FLO 200 | 10 g/l |

The pH of the activator solution was adjusted to 11.

The strips were developed for 90 sec, followed by 1 min in agitated EP-2 blix, then washed for 5 min in distilled water, dipped in PHOTO FLO 200, and dried.

The imaging activity and thermal stability of the exemplary blocked developing agents are given in Table V. The thermal stability denotes the percent retention, that is, the relative amount of blocked developing agent remaining after incubation, relative to the amount of developing agent initially coated.

TABLE V

| Example | Blocked Developer | Dmax − Dmin | Retention |
|---|---|---|---|
| 3 | 1 | 0.82 | 100% |
| 4 | 3 | 1.10 | 98% |
| 5 | 6 | 0.22 | 100% |

All of the exemplary blocked developers produced images under the above-described nucleophilic activation, and all exhibited a high degree of thermal stability.

EXAMPLES 6–9

Coatings of blocked developing agents 1 and 6 were exposed and processed without incubation at elevated temperature. Processing was carried out using activator solutions prepared with and without hydrogen peroxide. The activator solution with hydrogen peroxide was identical to that used in Examples 3–5, above. The activator solution without hydrogen peroxide was otherwise prepared identically as the solution of Examples 3–5, and subsequently adjusted to pH 11. The development, bleach-fix, washing and drying steps were essentially identical to those carried out in Examples 3–5.

Results are shown in Table VI.

TABLE VI

| Example | blocked developer | activator | Dmax − Dmin |
|---|---|---|---|
| 6 | 1 | $+H_2O_2$ | 0.62 |
| 7 | 1 | $-H_2O_2$ | 0.28 |
| 8 | 6 | $+H_2O_2$ | 0.15 |
| 9 | 6 | $-H_2O_2$ | 0.00 |

The use of hydrogen peroxide in an activator solution according to the invention clearly results in enhanced image formation.

It is to be understood that the foregoing detailed description and specific examples, while indicating preferred embodiments of the present invention, are given by way of illustration and not limitation. Many changes and modifications within the scope of the present invention may be made without departing from the spirit thereof, and the invention includes all such modifications.

What is claimed is:

1. A method for processing a photographic element comprising the steps of:
   (a) providing an imagewise exposed photographic element comprising a support, a silver halide emulsion containing an imagewise distribution of developable silver halide grains, and a blocked photographically useful compound comprising a photographically useful group and a blocking group capable of releasing said photographically useful group upon processing said photographic element in the presence of a peroxide, wherein said blocking group comprises an electrophilic group which is the sole group capable of undergoing a nucleophilic displacement reaction, said electrophilic group being bonded directly or through at least one releasable timing group to said photographically useful group,
   (b) color developing said imagewise exposed photographic element with a processing solution comprising a peroxide, and
   (c) bleaching or bleach/fixing said color developed photographic element.

2. The method of claim 1 wherein said processing solution used in step (b) is a color developing solution comprising a color developing agent.

3. The method of claim 1 wherein said blocked photographically useful compound in said photographic element is a blocked color developing agent.

4. The method of claim 1 further comprising a nonchromogenically developing step, and a uniformly fogging step, sequentially, before said color developing step.

5. A method as claimed in claim 1, wherein when said photographically useful group is a development inhibitor, said blocking group is bonded to said photographically useful group through at least two releasable timing groups.

6. A method as claimed in claim 1, wherein said photographically useful group is a photographically useful group other than a development inhibitor.

7. A method as claimed in claim 1, wherein said blocked photographically useful compound has the structure

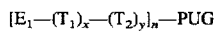

in which

E₁ is an electrophilic group,

T₁ and T₁ are individually releasable timing groups,

PUG is a photographically useful group capable of being released upon processing the photographically useful compound, x and y are independently 0 or 1, and n is 1 or 2.

8. A method as claimed in claim 7, wherein when PUG is a development inhibitor, the product n(x+y) is at least 2.

9. A method as claimed in claim 7, wherein said blocked photographically useful compound is represented by the formula

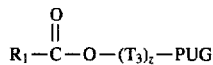

in which

R₁ is an unsubstituted or substituted alkyl, alkoxy, aryl or aryloxy group,

T₃ is a releasable timing group,

PUG is a photographically useful group capable of being released upon processing the photographically useful compound, and z is 0, 1 or 2.

10. A method as claimed in claim 9, wherein when PUG is a development inhibitor, z is 2.

11. A method as claimed in claim 1, wherein said blocking group is an acetyl, propionyl, pivalyl, butyryl, isobutyryl, pentanoyl or hexanoyl group.

12. A method as claimed in claim 9, wherein PUG is a coupler, dye, nucleating agent, development accelerator, inhibitor releasing developer, color developer, bleach inhibitor, silver halide solvent, silver ion fixing agent, silver halide complexing agent, pre-processing image stabilizer, postprocessing image stabilizer, hardener, antifoggant, ultraviolet radiation absorber, chemical sensitizer, chemical desensitizer, surfactant, or precursor thereof.

13. A method as claimed in claim 12, wherein PUG is a color developer.

14. A method as claimed in claim 8, wherein said development inhibitor is a phenylmercaptotetrazole.

15. A method as claimed in claim 1, wherein said peroxide has the structure

$R_2$—OOH in which $R_2$ is H, an unsubstituted or substituted alkyl, aryl, alkaryl, acyl, sulfonyl, oxycarbonyl or borate group.

16. A method as claimed in claim 15, wherein $R_2$ is a group which is hydrolyzable in alkaline solution, whereby said peroxide forms hydrogen peroxide.

17. A method as claimed in claim 15, wherein said peroxide is hydrogen peroxide, a salt thereof or a derivative thereof which is hydrolyzable to hydrogen peroxide in alkaline solution.

18. A method as claimed in claim 1, wherein said peroxide has the structure

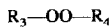

$R_3$—OO—$R_4$ in which each of $R_3$ and $R_4$ independently is an unsubstituted or substituted alkyl, aryl, alkaryl, sulfonyl, oxycarbonyl or borate group, or a group which is hydrolyzable in alkaline solution to yield the peroxy anion, with the proviso that at least one of $R_3$ and $R_4$ is a group that is hydrolyzable in alkaline solution to yield the peroxy anion.

19. A method as claimed in claim 18, wherein said peroxide is a salt of hydrogen peroxide or a derivative thereof which is hydrolyzable to hydrogen peroxide in alkaline solution.

* * * * *

UNITED STATES PATENT AND TRADEMARK OFFICE
CERTIFICATE OF CORRECTION

PATENT NO. : 5,538,834
DATED : July 23, 1996
INVENTOR(S) : Buchanan et al

It is certified that error appears in the above-indentified patent and that said Letters Patent is hereby corrected as shown below:

Col. 22, Line 45 [$T_1$ and $T_1$] replace therefor -- $T_1$ and $T_2$ --

Signed and Sealed this

Seventeenth Day of December, 1996

Attest:

BRUCE LEHMAN

Attesting Officer

Commissioner of Patents and Trademarks